United States Patent
Magri' et al.

(10) Patent No.: US 8,721,616 B2
(45) Date of Patent: May 13, 2014

(54) PACKAGING SYSTEM FOR PHARMACEUTICAL COMPOSITIONS AND KIT FOR INTRAVENOUS ADMINISTRATION

(75) Inventors: Paolo Magri', Corteglia (CH); Flavio Villani, Parma (IT)

(73) Assignee: Infa S.A., Mendrisio (CH)

( * ) Notice: Subject to any disclaimer, the term of this patent is extended or adjusted under 35 U.S.C. 154(b) by 504 days.

(21) Appl. No.: 12/443,058

(22) PCT Filed: Sep. 28, 2007

(86) PCT No.: PCT/IB2007/002857
§ 371 (c)(1),
(2), (4) Date: Apr. 16, 2009

(87) PCT Pub. No.: WO2008/038126
PCT Pub. Date: Apr. 3, 2008

(65) Prior Publication Data
US 2010/0030182 A1 Feb. 4, 2010

(30) Foreign Application Priority Data

Sep. 29, 2006 (IT) .............................. MI2006A1881
Mar. 29, 2007 (IT) .............................. MI2007A0635

(51) Int. Cl.
*A61B 19/00* (2006.01)
(52) U.S. Cl.
USPC ......................... 604/416; 604/403; 604/415
(58) Field of Classification Search
USPC .................................................. 604/403–416
See application file for complete search history.

(56) References Cited

U.S. PATENT DOCUMENTS

| 3,194,237 | A | 7/1965 | Rubin | |
|---|---|---|---|---|
| 3,369,708 | A | 2/1968 | Hein | |
| 3,900,028 | A * | 8/1975 | McPhee | 604/415 |
| 6,364,865 | B1 * | 4/2002 | Lavi et al. | 604/411 |
| 2002/0013340 | A1 | 1/2002 | Peyman | |
| 2002/0188281 | A1 * | 12/2002 | Dellamary et al. | 604/890.1 |
| 2004/0039366 | A1 * | 2/2004 | MacLeod | 604/416 |
| 2005/0155901 | A1 | 7/2005 | Krueger et al. | |
| 2008/0228161 | A1 * | 9/2008 | Claussen et al. | 604/404 |

FOREIGN PATENT DOCUMENTS

| EP | 0 459 182 | 12/1991 |
|---|---|---|
| EP | 0 598 918 | 6/1994 |
| EP | 1 093 784 | 4/2001 |
| GB | 832350 | 4/1960 |
| WO | WO 2005/030205 | 4/2005 |
| WO | WO 2006/066030 | 6/2006 |

OTHER PUBLICATIONS

International Search Report for PCT/IB2007/002857, mailed Aug. 25, 2008.
Written Opinion of the International Searching Authority for PCT/IB2007/002857, mailed Aug. 25, 2008.

* cited by examiner

*Primary Examiner* — Leslie Deak
(74) *Attorney, Agent, or Firm* — Nixon & Vanderhye P.C.

(57) ABSTRACT

The invention refers to a new system for packaging pharmaceutical compositions comprising active principles that may be administered intravenously, in particular it concerns a system for packaging in bottles which makes it possible to ensure the complete transfer of the content of the bottle into the liquid for intravenous infusion and at the same time prevent any accidental contact with the active principle by the health-care personnel preparing said intravenous infusion, and a complete kit for intravenous administration.

12 Claims, 1 Drawing Sheet

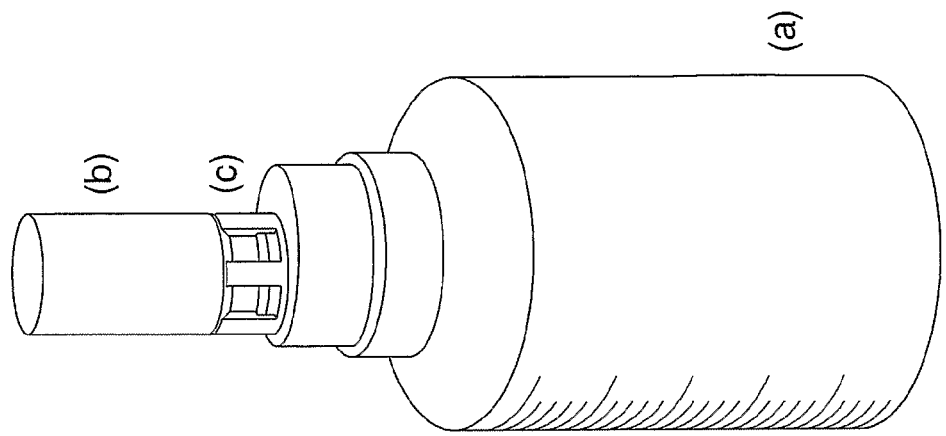
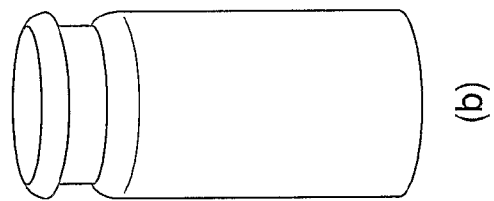
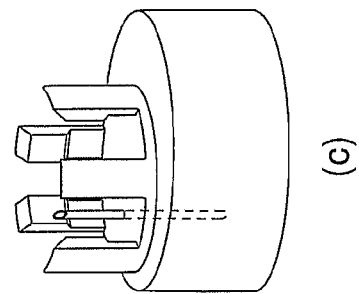

PACKAGING SYSTEM FOR PHARMACEUTICAL COMPOSITIONS AND KIT FOR INTRAVENOUS ADMINISTRATION

This application is the U.S. national phase of International Application No. PCT/IB2007/002857, filed 28 Sep. 2007, which designated the U.S. and claims priority to Italy Application No. MI2006A001881, filed 29 Sep. 2006, and Italy Application No. MI2007A000635, filed 29 Mar. 2007, the entire contents of each of which are hereby incorporated by reference.

SUMMARY OF THE INVENTION

The present invention refers to a new system for packaging pharmaceutical compositions comprising active principles that may be administered intravenously, in particular it concerns a system for packaging in bottles which makes it possible to ensure the complete transfer of the content of the bottle into the liquid for intravenous infusion and at the same time prevent any accidental contact with the active principle by the health-care personnel preparing said intravenous infusion. More particularly, the invention refers to a new system for packaging pharmaceutical compositions comprising Tacrolimus and other highly active drugs.

The invention concerns a kit for the parenteral administration of medicines which comprises said packaging system.

TECHNICAL CONTEXT

Some highly active drugs, such as anti-tumour, immunosuppressants, antiviral drugs, some hormone derivatives, are considered potentially dangerous for the health-care personnel who have to handle them at the time or administration. For this reason, in the United States, the NIOSH (National Institute for Occupational Safety and Health) publishes guidelines for protecting the health and safety of health-care workers (www.cdc.aov/niosh) and lists the dangerous active principles for which particular attention is required during administration, such as the use of gloves and eye protection when opening the drug package (vial or similar).

In many cases these drugs are administered intravenously, either because of the intrinsic characteristics of the active principle or when the patient's conditions do not allow them to be administered by mouth.

The pharmaceutical compositions intended for intravenous administration must be transferred from the pack in which they are sold into a suitable container holding the liquid for infusion. The transfer is generally made by taking said compositions (when possible already in a solution or to be dissolved or diluted with an appropriate solvent at the moment of use) by means of a syringe and injecting the liquid composition thus obtained into the container holding the liquid for infusion. This type of transfer presents several inconveniences, including the risk for the health-care personnel of accidental pricking or of contact with the drug which, as explained above, may be extremely toxic or dangerous. Said transfer also presents the risk of losing part of the drug to be administered, which often remains in the package, as it is difficult to extract a liquid completely with a syringe, for example from an ampoule. This possibility, which is quite frequent, may have extremely serious consequences. For this reason pharmaceutical companies tend to minimise the risk of administering too little with respect to the prescribed amount by means of "overdosing", that is adding an extra quantity of active principle to the pharmaceutical composition too be sold. This overdosing is generally around 10%, but in some particular cases it may be as much as 20%. Besides the waste of active principles, often extremely expensive, this solution involves an opposite risk, that is the danger of administering to the patient an amount of drug higher than that necessary for the therapy. It can easily be understood that, especially for highly active drugs, this risk is unacceptable for the patient's health.

Another problem connected with the use of ampoules lies in the cost and complexity of production. The process for producing ampoules is in fact much more expensive than that of producing bottles and involves risks linked with the flammability of the solvents used as vehicles for the active principles.

Technology has recently developed means for trying to overcome at least part of the inconveniences listed above. In particular, connectors equipped with at least two perforating spikes (known as spikes) have been designed and marketed, suited to put directly into connection the container holding the liquid for infusion and the package of the pharmaceutical composition, which in this case is generally a bottle sealed with an appropriate rubber cap. These connectors therefore perforate the cap of the container holding the liquid for infusion on one side and the cap of the bottle holding the composition on the other and said composition can be transferred by means of the so-called wash-out of the bottle by the liquid for infusion which is pushed upwards by compression of the infusion container, which in this case is made of collapsible material. These means are marketed for example by the company B.Braun Melsungen AG, Germany.

This combination makes it possible to avoid the inconvenience related to the risk of accidental pricking or of contact with the drug for health-care personnel, but it does not actually solve the problem of the complete transfer of the pharmaceutical composition into the liquid to be administered by infusion, nor the problem of overdosing of the drug.

In fact, in pharmaceutical compositions for infusion, in particular those including the highly active drugs mentioned above, the active principles are often dissolved using lipophilic substances and they do not dissolve easily in conventional liquids for infusion; it has been verified that the transfer by "washing out" the bottle with the liquid for infusion, which is of necessity composed of an aqueous solution mixable with said lipophilic substances, is often incomplete.

OBJECTS OF THE INVENTION

The object of the present invention is to overcome all the inconveniences of the known technique, providing a system for packaging in bottles pharmaceutical compositions comprising active principles that may be administered intravenously and a complete kit for its use, which makes it possible to ensure the complete transfer of the content of the bottle into the liquid for intravenous infusion and which is safe for the health-care personnel who have to administer it.

Another object of the present invention is to reduce the costs and the dangers indicated above, connected with the production of ampoules.

Another object of the present invention is to provide a system for packaging in bottles Tacrolimus and other drugs that may be administered intravenously and a complete kit for its use, which at the same time makes it possible to safeguard the health of the health-care personnel and to administer the exact quantity of the necessary active principle, reducing both the waste of expensive drugs and the risk of overdosing for the patient.

It has surprisingly been observed that the size of the bottle is of critical importance for the correct transfer of the pharmaceutical composition that it contains into the container for infusion. It has in fact been found that the identification of a suitable size of the bottle is indispensable for the "washing out" described above to be effective for the complete transfer of the drug.

The authors of the present invention have highlighted, for the first time, the fundamental role played by the size of the bottle for the efficacy of the transfer of the pharmaceutical composition to be transferred into a liquid for infusion using the system described above, with particular reference to Tacrolimus and other drugs dissolved in lipophilic substances and that do not dissolve easily in the liquids for infusion. This critical aspect had never been considered before in the prior art.

It has now unexpectedly been observed that the washing out of a bottle of the type described above, containing a pharmaceutical composition to be administered in a liquid for intravenous infusion, is much more effective when the size of said bottle is calculated in such a way as to allow a large empty volume, that is if it is not almost entirely filled with the pharmaceutical composition. This observation is in sharp contrast with the current practices of pharmaceutical technology, which tend to leave very little empty volume inside the package of a pharmaceutical composition, above all if of a liquid type. For example, the active principle Tacrolimus is sold in ampoules with a capacity of only 2 ml, which contain 1 ml of pharmaceutical composition, so they are half full.

DESCRIPTION OF THE INVENTION

So, according to one of its aspects, the invention concerns a packaging system for holding a pharmaceutical composition to be administered in a liquid for intravenous infusion, characterised in that said packaging system is a bottle which comprises said pharmaceutical composition and an empty volume of more than 80% of the total volume of the bottle, preferably ranging from 80% to 99%, advantageously from 80% to 95%, for example which is around 85% of the total volume of the bottle. According to the present invention, the term "pharmaceutical composition" means a drug formulated with one or more pharmaceutically acceptable vehicles, ready for transfer into the liquid for intravenous infusion. So, in the case of drugs which require pre-dilution with a cosolvent prior to transfer into the liquid for intravenous infusion, for example docetaxel, the term "pharmaceutical composition" means the mixture of the concentrate with the cosolvent.

According to the present invention, the term "liquid for intravenous infusion" means any conventional solution for intravenous infusion, for example a saline physiological solution or a physiological solution containing glucose.

According to the present invention, the term "bottle" means a container holding a pharmaceutical composition, closed with a rubber cap, which may be pierced with needles or conventional piercing spikes. These bottles are available on the market in different sizes.

According to the present invention, the dimensions of the bottle are defined as "capacity", where the term "capacity" indicates the volume of the bottle available as generally indicated by the manufacturer and not the "to the brim" volume of the bottle. So, according to the present invention, when mentioning for example a 7 ml bottle, it means a bottle that the manufacturer declares has a capacity of 7 ml but which, when "brim full", contains even more than 8 ml, for example 8.4.

According to an advantageous embodiment of the invention, said bottle shall be made of glass, transparent or amber-coloured depending on the light-sensitivity of the active principle, and preferably it shall have an opening of the DIN/ISO type (about 22 mm), a characteristic which allows good compatibility with the majority of conventional connectors.

According to the present invention, the term "empty volume" (or also head space) means the volume inside the bottle not occupied by the pharmaceutical composition. The empty volume percentages are given here in terms of a percentage with respect to the capacity of the bottle, in such a way that the sum of the percentage of the volume of the composition and of the percentage of the empty volume is always 100%.

According to a preferred aspect of the present invention, said empty volume is chosen as a function of the solubility of the active principle and/or of the composition. According to a preferred aspect of the present invention, said pharmaceutical composition is a pharmaceutical composition comprising a highly active drug dissolved in a lipophilic substance.

According to a preferred aspect of the present invention, said pharmaceutical composition is a pharmaceutical composition comprising a highly active drug dissolved in a lipophilic substance.

According to a particularly preferred embodiment of the invention, said pharmaceutical composition is a pharmaceutical composition comprising a drug chosen among immunosuppressants, anti-tumour drugs and hormones.

According to a particularly preferred embodiment of the invention, said pharmaceutical composition is a pharmaceutical composition comprising a drug chosen among tacrolimus, cyclosporine, alkylating agents (carmustine, busulfan), docetaxel, paclitaxel, teniposide, pentamidine and valrubicin.

According to another of its aspects, the invention concerns a packaging system for a pharmaceutical composition to be administered in a liquid for intravenous infusion characterised in that said packaging is a bottle having a capacity between 5 and 10 ml and said pharmaceutical composition comprises as active principle tacrolimus in a pharmaceutically acceptable oily vehicle.

According to a particularly preferred embodiment of this last aspect of the invention, said pharmaceutical composition comprises 5 mg of tacrolimus dissolved in 1 ml of solvent composed of 260 mg of polyoxyethylenated hydrogenated castor oil (HCO-60) and ethanol, for example absolute ethanol or anhydrous ethanol USP 80.0% v/v, q.s. to 1 ml.

According to a particularly preferred embodiment of the invention, said pharmaceutical composition comprises from 0.1 to 0.5 mg, preferably about 0.25 mg of citric acid, 5 mg of tacrolimus dissolved in 1 ml of solvent composed of 200 mg of polyoxyethylenated hydrogenated castor oil (HCO-60) and ethanol, for example absolute ethanol or anhydrous ethanol USP 80.0% v/v, q.s. to 1 ml According to another particularly preferred embodiment the pharmaceutical compositions comprising as active principle 5 mg of tacrolimus, with or without citric acid, are contained in a bottle having a capacity from 6 to 9 ml, advantageously of 7 ml, the empty space therefore amounting to 85.7%.

If necessary or desired, the pharmaceutical compositions may be packed according to the system of the invention in an inert atmosphere, for example in an atmosphere of nitrogen, argon or $CO_2$.

For the use of the packaging system of the invention, the bottle in used in combination with connectors provided with at least two perforating spikes (known as spikes), suited to put the inside of the bottle directly in contact with the container holding the liquid for infusion. The container for infusion shall be made of collapsible material and advantageously compatible with the pharmaceutical composition and the active principle to be administered, for example in a material other than PVC if oily vehicles are used or drugs incompatible with PVC.

According to the present invention, the term "collapsible material" means a material that may be manually compressed to make the liquid for infusion come out through the spikes of the connector described above.

FIG. 1 shows a particularly advantageous embodiment of the kit of the invention, at the moment of transfer of the pharmaceutical composition from the dosage unit (b) to the container (a) by means of a connector with two spikes (c).

In practice, a container holding a liquid for infusion as defined above is engaged on one end of a connector equipped with at least two spikes, one of which penetrates inside the rubber cap of said container; then a bottle of the packaging system of the invention, after removal of the metal cap usually present on top of the rubber cap, is engaged, upside down, on the other end of the above-mentioned connector, causing the perforation of the rubber cap.

By applying a light pressure on the container in collapsible material, the liquid for infusion passes through the two spikes and flows into the bottle, "washing it out" (FIG. 1).

If the packaging system of the invention has been conveniently realised, that is suitably choosing the capacity of the bottle, only one wash is sufficient to transfer more than 99% of the active principle contained in said bottle. Always in optimal conditions, if two washes are performed, practically 100% of the active principle is certainly transferred.

The connectors used in combination with the packaging system of the invention are known to the technique and available on the market, for example sold by the company B.Braun Melsungen AG, Germany.

According to a preferred embodiment, said spikes have a length such that they do not penetrate much inside said bottles, to avoid leaving any residual volume of pharmaceutical composition mixed with solution for infusion inside the bottle itself. The containers holding the liquid for infusion made of collapsible material are known and marketed by many companies. These containers may be in the shape of bags or bottles.

So, according to one of its aspects, the present invention concerns a kit for the parenteral administration of drugs which comprises at least:
a) a container holding a fluid for parenteral infusion;
b) a dosage unit comprising at least one pharmaceutical composition in liquid form to be parenterally administered;
c) a means for transferring the pharmaceutical composition from the dosage unit (b) to the container (a);
characterised in that said at least one dosage unit is a packaging system according to the invention.

According to the present invention, the term "parenteral administration" means any administration by an approach other than oral, and includes principally, but not only, intravenous administration.

The "container" referred to as component (a) is for example an infusion bag or a glass bottle and it contains a "fluid for parenteral infusion" which is a solution or a microemulsion for infusion, for example a physiological solution containing salts, sugars, etc., or a microsuspension, for example of the type for parenteral feeding, all advantageously sterile.

The "container" of the invention also comprises the couplings, tubes, flow regulators, any filters or dosers, and all the material for transferring the fluid for parenteral infusion, advantageously for intravenous infusion, such as needles, butterfly valve, etc.

According to the present invention, the term "means for transferring the pharmaceutical composition" indicates any instrument suited for transferring the pharmaceutical composition from the dosage unit (b) to the container (a). Preferably the means for transferring the pharmaceutical composition may be composed of a suitable coupling which puts said dosage unit in communication with said container. According to a particularly preferred aspect, said means for transferring the pharmaceutical composition is a connector provided with at least two perforating spikes (known as spikes), suited to put the inside of the bottle directly in contact with the container holding the liquid for infusion.

The kit of the invention may also advantageously comprise disposable gloves and an illustrative leaflet, as well as labels giving the necessary warnings for the health-care operator.

The fluid for parenteral infusion contained in the container (a) must also be compatible with the drug to be administered. For example, in the case of drugs that do not tolerate infusion solutions with determined pH values or containing specific vehicles, the fluid for parenteral infusion shall be suitably chosen so as to avoid all possible degradation or alteration of the active principle.

It may therefore be understood that the kit of the invention, containing all the necessary parts for intravenous administration, suitably chosen according to the nature of the drug and of the pharmaceutical composition to be administered, puts health-care personnel in conditions in which they can work safely and quickly.

According to one embodiment of the invention, the infusion fluid is a solution for intravenous infusion and contains a solution for injection of 0.9% sodium chloride (saline solution) or 5% dextrose (glucose solution).

According to another embodiment of the invention, the kit comprises two containers (a) one of which contains a saline solution and the other a glucose solution as described above. This variation allows the health-care operator, if he wishes, to choose the infusion solution most useful for the treatment at that moment.

According to a particularly preferred embodiment the invention concerns a kit as defined above, wherein said pharmaceutical composition comprises tacrolimus as the active principle.

According to a particularly advantageous embodiment the invention concerns a kit as defined above, wherein said one dosage unit is a bottle containing a pharmaceutical composition which comprises 5 mg of tacrolimus dissolved in 1 ml of solvent composed of 200 mg of polyoxyethylenated hydrogenated castor oil (HCO-60) and ethanol, for example absolute ethanol or anhydrous ethanol USP 80.0% v/v, q.s. to 1 ml, said bottles having a capacity comprises between 5 and 10 ml, preferably between 6 and 9 ml, advantageously of about 7 ml.

According to another advantageous embodiment the invention concerns a kit as defined above, wherein said dosage unit is a bottle containing a pharmaceutical composition which comprises from 0.1 to 0.5 mg of citric acid, preferably about 0.25 mg, and 5 mg of tacrolimus dissolved in 1 ml of solvent composed of 200 mg of polyoxyethylenated hydrogenated castor oil (HCO-60) and ethanol, for example absolute ethanol or anhydrous ethanol USP 80.0% v/v, q.s. to 1 ml According to an advantageous embodiment the invention concerns a kit which comprises at least:
a) a container holding a fluid for parenteral infusion;
b') a dosage unit in the form of a bottle with a capacity of about 7 ml, comprising at least one pharmaceutical composition composed of 5 mg of tacrolimus dissolved in 1 ml of solvent composed of 200 mg of polyoxyethylenated hydrogenated castor oil (HCO-60) and ethanol, for example absolute ethanol or anhydrous ethanol USP 80.0% v/v, q.s. to 1 ml.

c) a means for transferring the pharmaceutical composition from the dosage unit (b') to the container (a).

According to an advantageous embodiment the invention concerns a kit which comprises at least:
- a collapsible container for intravenous infusion containing 500 ml of a saline solution of 0.9% sodium chloride, catheter and butterfly needle, the whole being made of PE;
- a bottle having a capacity of about 7 ml, containing a pharmaceutical composition composed of 5 mg of tacrolimus dissolved in 1 ml of solvent composed of 200 mg of polyoxyethylenated hydrogenated castor oil (HCO-60) and ethanol q.s. to 1 ml;
- a connector with at least two perforating spikes;
- a pair of disposal gloves for pharmaceutical use;
- an illustrative leaflet concerning on the active principle tacrolimus.

According to another of its aspects, the invention concerns a method for transferring a pharmaceutical composition into a solution for intravenous infusion, said method comprising:
- engaging a container holding a liquid for intravenous infusion, made of collapsible material, on one end of a connector equipped with at least two spikes, one of which penetrates inside the rubber cap of said container;
- engaging a bottle of the packaging system of the invention, after removal of the metal cap usually present on top of the rubber cap, upside down, on the other end of the above-mentioned connector, causing the perforation of the rubber cap;
- applying a light pressure on the container in collapsible material to make the liquid for infusion pass through the two spikes and allow said bottle to be "washed out";
- optionally repeating the operation in the previous step.

According to a particularly preferred embodiment the invention concerns a method as defined above, wherein said pharmaceutical composition comprises tacrolimus as the active principle.

The invention also concerns the use of a packaging system as defined above for intravenous administration of a pharmaceutical composition.

The packaging system of the invention may also be used for drugs that require pre-dilution before being transferred into the container holding the liquid for infusion, for example docetaxel.

In the specific case of docetaxel, for example, the pharmaceutical speciality on the market comprises a bottle containing the active principle in polysorbate 80 and a bottle containing a solvent with which further to dilute the active principle before transfer into the liquid for infusion. Dilution is carried out by the health-care personnel using a syringe. The illustrative leaflet of the medicinal speciality clearly specifies the conditions for making the dilution, so that a precipitate is not formed by rubbing the walls of the bottle with the transfer needle, as the final solution is oversaturated.

Once diluted, the pharmaceutical composition thus formed is normally lifted with a syringe and transferred into the container holding the liquid for infusion. For the reasons discussed above, the active principle is present in the speciality in excess of more than 10%, even of 20%, with respect to the declared amount.

The present invention not only succeeds in overcoming the inconveniences linked with the transfer of the pharmaceutical composition into the infusion container, but it also provides a pre-dilution system which preserves the health-care personnel from accidental contact with the needle of the used syringe or from the possible precipitation of some active principles which require said pre-dilution.

So, according to another of its aspects, the invention supplies a kit comprising:
(i) a packaging system as defined above suitable for a pharmaceutical component comprising docetaxel,
(ii) a bottle containing the solvent or the mix of suitable solvents for pre-dilution of a docetaxel concentrate; and
(iii) means for pre-diluting the concentrate with the solvent or the mix of suitable solvents.

The above means (iii) include for example a syringe with a retractable safety needle; a syringe with a shielded needle (guard) which is activated with only one hand; a syringe with a plastic needle, suitable for perforating rubber (safer than a steel needle); a syringe without a needle but with a Luer-Lock type connection (male) or similar, coupled to a connector having a spike on one side (facing the bottle) and a Luer-Lock or similar connection (female) on the other side.

According to a particular embodiment of this aspect of the invention, the bottle (ii) is not present and said solvent or said mix of solvents for pre-dilution are contained in the means (iii) in which said syringes are therefore pre-filled.

It this way it is possible for the health-care personnel to take and transfer said solvent or said mix of solvents safely and at the same time eliminate the risk of precipitation of the active principle.

As has been said, it has been demonstrated that the efficacy of transfer depends directly on the packaging system used, in particular on the ratio between the volume of the pharmaceutical composition and the empty volume in the bottle.

For example, washing tests have been carried out on various types of packaging systems comprising a bottle containing a pharmaceutical composition containing 5 mg of tacrolimus dissolved in 1 ml of solvent composed of 200 mg of polyoxyethylenated hydrogenated castor oil (HCO-60) and ethanol, for example absolute ethanol or anhydrous ethanol USP 80.0% v/v, q.s. to 1 ml.

In particular bottles containing the above composition but having different capacities were tested, that is bottles with capacity from 3 to 15 ml.

In the test the washing-out manoeuvres described above were performed and the residual amount of tactrolimus in the bottle after one or two washes was assessed.

The results of the test are shown below in TABLE I.

TABLE I

| Bottle capacity ml | Quality of connection | Number of washes | [TAC] in residual volume (*) | Number of washes | [TAC] in residual volume (*) |
|---|---|---|---|---|---|
| 3 | Not very stable | One | >8% | Two | >2% |
| 5 | Reasonably stable | One | >5% | Two | ~1% |
| 7 | Very stable | One | <1% | Two | Traces |
| 8 | Very stable | One | <1% | Two | Traces |
| 9 | Stable | One | <1% | Two | Traces |

TABLE I-continued

| Bottle capacity ml | Quality of connection | Number of washes | [TAC] in residual volume (*) | Number of washes | [TAC] in residual volume (*) |
|---|---|---|---|---|---|
| 10 | Reasonably stable | One | <1% | Two | Traces |
| 15 | Reasonably stable | One | <1% | Two | Traces |

(*) concentration of tacrolimus in the residual liquid.

It is clear from the data given in the table that the optimal capacity of the bottle containing the pharmaceutical composition of tacrolimus defined above is between 5 and 10 ml.

For the purposes of efficacy of washing out, even bottles with a larger capacity could be use, but in this case there is some loss in terms of stability of connection.

The stability of connection factor is in fact equally important, since the difference in pressure is decisive for limiting the volume that remains in the bottle and so it is fundamental for this connection to be hermetic. The stability of connection is strongly influenced by the shape of the neck of the bottle and by its consequent capacity to adapt to the connector.

For this reason, in the test described above, with the same percentage content of active principle in the residual volume, that is in the very small volume of liquid that remains in the bottle, bottles with a capacity of less than 10 ml are preferable because they allow a more stable connection.

However, bottles with larger dimensions were also tested, up to 50 ml. These bottles have shown that they can achieve a sufficiently stable connection and an adequate "wash-out" but, as is understandable, they cannot reasonably be considered appropriate for containing 1 ml of pharmaceutical composition, also because in this way the possibility of making and effective visual control is lost.

The bottles thus prepared and used in the test described above were subjected to a stability test and the results showed a correct stability of the composition.

We have therefore shown how the packaging system described above, in particular with reference to bottles containing a pharmaceutical composition composed of 5 mg of tacrolimus dissolved in 1 ml of solvent composed of 200 mg of polyoxyethylenated hydrogenated castor oil (HCO-60) and ethanol, for example absolute ethanol or anhydrous ethanol USP 80.0% v/v, q.s. to 1 ml, said bottles having a capacity between 5 and 10 ml, overcomes all the inconveniences of the prior art, above all considering the fact that at present the only pharmaceutical composition containing tacrolimus available on the market is packed in an ampoule to be opened by breaking the neck and to be transferred by taking it with a syringe.

It is clear that the kit of the invention also allows the possibility of later connecting several packaging systems (bottles) of the invention to the same infusion bag, thus making it possible, by means of a series of charges (washes), to arrive at the desired concentration of the drug in the infusion bag easily and without risks for the health-care personnel. At present health-care operators often take doses of active principle from several bottles or ampoules, therefore using numerous syringes with a needle, in order to reach the specific concentration desired for a given patient. The kit of the invention is therefore an important technical progress in favour of safety in the health-care environment.

The advantages of the packaging system of the invention, in particular of the one containing tacrolimus examined above in detail, therefore seem evident and confirm the important technical progress offered by the invention.

EXPERIMENTAL SECTION

Examples

Example 1

Kit for Intravenous Administration of Tacrolimus

A kit is prepared in the form of a pharmaceutical package containing
   a collapsible container for intravenous infusion containing 500 ml of a saline solution of 0.9% sodium chloride, coupling and butterfly needle, the whole being made of PE;
   a bottle having a capacity of about 7 ml, containing a pharmaceutical composition composed of 5 mg of tacrolimus dissolved in 1 ml of solvent composed of 200 mg of polyoxyethylenated hydrogenated castor oil (HCO-60) and ethanol q.s. to 1 ml;
   a connector with at least two perforating spikes;
   a pair of disposal gloves for pharmaceutical use;
   an illustrative leaflet concerning on the active principle tacrolimus.

Examples 2-5

A kit in the form of a pharmaceutical package like the one in example 1 may contain different types of pharmaceutical compositions such as:

Example 2

A pharmaceutical composition composed of 5 mg of anhydrous tacrolimus dissolved in 1 ml of solvent composed of 200 mg of polyoxyethylenated hydrogenated castor oil (HCO-60) in dehydrated ethanol (USP 80.0% v/v) q.s. to 1 ml.

Example 3

A pharmaceutical composition composed of 5 mg of anhydrous tacrolimus dissolved in 1 ml of solvent composed of 200 mg of polyoxyethylenated hydrogenated castor oil (HCO-60), 0.25 mg citric acid, in dehydrated ethanol (USP 80.0% v/v) q.s. to 1 ml.

Example 4

A pharmaceutical composition composed of 5 mg of anhydrous tacrolimus dissolved in 1 ml of solvent composed of 200 mg of polyoxyethylenated hydrogenated castor oil (HCO-60), 0.25 mg monohydrate citric acid, in dehydrated ethanol (USP 80.0% v/v) q.s. to 1 ml.

Example 5

A pharmaceutical composition composed of 2.5 mg of anhydrous tacrolimus dissolved in 0.5 ml of solvent composed of 100 mg of polyoxyethylenated hydrogenated castor oil (HCO-60), 0.125 mg monohydrate citric acid, in dehydrated ethanol (USP 80.0% v/v) q.s. to 0.5 ml.

Example 6

Kit for Intravenous Administration of Docetaxel

A kit is prepared in the form of a pharmaceutical package containing
- a collapsible container for intravenous infusion containing 500 ml of a saline solution of 0.9% sodium chloride and/or a solution of 5% dextrose, coupling and butterfly needle, the whole being made of PE;
- a bottle having a capacity of about 24 ml, containing a concentrate composed of 40 mg of docetaxel dissolved in 1 ml of polysorbate 80;
- a pre-filled syringe containing 3 ml of a solution of 13% ethanol in water;
- a connector with at least two perforating spikes;
- a pair of disposal gloves for pharmaceutical use;
- an illustrative leaflet concerning on the active principle docetaxel.

Example 7

A kit in the form of a pharmaceutical package like the one in example 6 may also contain a concentrate of docetaxel composed of 100 mg of active principle in 2.5 ml of polysorbate 80 in a bottle having a capacity of 60 ml and a pre-filled syringe containing 7.5 ml of a solution of 13% ethanol in water.

The invention claimed is:

1. A packaging system comprising:
   a container comprising collapsible material that holds a liquid for intravenous infusion;
   a pharmaceutical composition adapted to be transferred to the container; and
   a bottle comprising said pharmaceutical composition, the bottle having a capacity between 5 ml and 10 ml and an empty volume ranging from 80% to 99% of the total volume of the bottle,
   wherein said pharmaceutical composition comprises 5 mg of tacrolimus dissolved in 1 ml of solvent composed of 200 mg of polyoxyethylenated hydrogenated castor oil (HCO-60) and ethanol.

2. A packaging system according to claim 1, wherein said bottle comprises an empty volume ranging from 80% to 95% of the total volume of the bottle.

3. A packaging system according to claim 1, wherein said bottle is a container for pharmaceutical compositions closed with a rubber cap, said cap being able to be pierced with needles or conventional piercing spikes.

4. A packaging system according to claim 1, wherein said bottle is made of glass.

5. A packaging system according to claim 1, wherein said bottle has a capacity between 6 and 9 ml.

6. A packaging system according to claim 5, wherein said bottle has a capacity of 7 ml.

7. A packaging system comprising:
   a pharmaceutical composition adapted to be administered in a liquid for intravenous infusion; and
   a bottle adapted to store said pharmaceutical composition with an empty volume ranging from 80% to 99% of the total volume of the bottle,
   wherein said pharmaceutical composition comprises 5 mg of tacrolimus dissolved in 1 ml of solvent composed of 200 mg of polyoxyethylenated hydrogenated castor oil (HCO-60) and ethanol.

8. A packaging system according to claim 7, wherein said bottle comprises an empty volume ranging from 80% to 95% of the total volume of the bottle.

9. A packaging system according to claim 7, wherein said bottle is a container for pharmaceutical compositions closed with a rubber cap, said cap being able to be pierced with needles or conventional piercing spikes.

10. A packaging system according to claim 7, wherein said bottle is made of glass.

11. A packaging system according to claim 7, wherein said bottle has a capacity between 5 ml and 10 ml.

12. A packaging system according to claim 7, further comprising a container to which the pharmaceutical composition from the bottle is to be transferred, wherein said container comprises collapsible material.

* * * * *